United States Patent [19]
Majchrowski

[11] Patent Number: 5,457,278
[45] Date of Patent: Oct. 10, 1995

[54] PUMPKIN VARIETY RS 1090

[75] Inventor: Robert L. Majchrowski, Jackson, Mich.

[73] Assignee: Rupp Seeds Inc., Wauseon, Ohio

[21] Appl. No.: 228,331

[22] Filed: Apr. 15, 1994

Related U.S. Application Data

[63] Continuation of Ser. No. 981,325, Nov. 24, 1992, abandoned.

[51] Int. Cl.$^6$ .............................. A01H 5/00; A01H 5/08; A01H 5/10
[52] U.S. Cl. .................. 800/200; 800/255; 800/DIG. 20; 47/58; 47/DIG. 1
[58] Field of Search ..................................... 800/200, 255, 800/DIG. 20; 47/58.03, DIG. 1; 435/240.4

OTHER PUBLICATIONS

Jelaska et al. 1985, Physiol. Plant. 64:237–242.
Asgrow Vegetable Grower's Guide 1982. p. 52.
Ammirato. 1983. In Handbook of Plant Cell Culture. Evans et al., eds. vol. 1:82, 85, 88–93, 116.
Burpee Gardens Catalog. 1988. p. 149.
Whitaker et al. 1986. In Breeding Vegetable Crops. Bassett, ed. Ch. 6:209–242.
Hu et al. 1986. In Handbook of Plant Cell Culture. Evans et al., eds. vol. 4:76–79, 88.

*Primary Examiner*—Gary Benzion
*Assistant Examiner*—Erich E. Veitenheimer
*Attorney, Agent, or Firm*—Henderson & Sturm

[57] ABSTRACT

A novel pumpkin variety, designated RS1090, is disclosed. The invention relates to the seeds of pumpkin variety RS1090, to the plants of pumpkin variety RS1090 and to methods for producing a pumpkin plant produced by crossing the variety RS1090 with itself or another pumpkin line. The invention further relates to hybrid pumpkin seeds and plants produced by crossing the variety RS1090 with another pumpkin line.

7 Claims, No Drawings

PUMPKIN VARIETY RS 1090

CROSS REFERENCE TO RELATED APPLICATION

This application is a continuation of application Ser. No. 07/981,325 filed Nov. 24, 1992, now abandoned.

BACKGROUND OF THE INVENTION

The present invention relates to a new and distinctive pumpkin variety, designated RS1090. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, tolerance to drought and heat, and better quality.

Choice of breeding or selection methods depends on the mode of plant reproduction, the heritability of the trait(s) being improved, and the type of cultivar used commercially (e.g., $F_1$ hybrid, variety, etc.). For highly heritable traits, a choice of superior individual plants evaluated at a single location may be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s). The best lines are candidates for new commercial cultivars; those still deficient in a few traits are used as parents to produce new populations for further selection.

These processes, which lead to the final step of marketing and distribution, usually take from ten to 30 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior pumpkin varieties and hybrids. The breeder initially selects and crosses two or more parental lines, followed by repeated selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same variety twice by using the exact same original parents and the same selection techniques. This unpredictability results in the expenditure of large research monies to develop superior new pumpkin varieties.

The development of commercial pumpkin hybrids requires the development of varieties, the crossing of these varieties, and the evaluation of the crosses. Pedigree breeding and recurrent selection breeding methods are used to develop varieties from breeding populations. Breeding programs combine desirable traits from two or more varieties or various broad-based sources into breeding pools from which varieties are developed by crossing and selection of desired phenotypes. The new varieties are crossed with other varieties and the hybrids from these crosses are evaluated to determine which have commercial potential.

Pedigree breeding is used commonly for the improvement of both self-pollinating and cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987, Basset, 1986).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the varieties that give the best hybrid performance have been identified, the hybrid seed can be reproduced indefinitely as long as the homogeneity of the parent is maintained. A single-cross hybrid is produced when two varieties are crossed to produce the $F_1$ progeny. A double-cross hybrid is produced from four varieties crossed in pairs (A×B and C×D) and then the two $F_1$ hybrids are crossed again (A×B)×(C×D). Much of the hybrid vigor exhibited by $F_1$ hybrids is lost in the next generation ($F_2$).

Pumpkin is an important and valuable crop. Thus, a continuing goal of plant breeders is to develop stable, high yielding pumpkins that are agronomically sound. The reasons for this goal are obviously to maximize the total yield and quality produced on the land used. To accomplish this goal, the pumpkin breeder must select and develop pumpkin plants that have the traits that result in superior varieties and hybrids.

SUMMARY OF THE INVENTION

According to the invention, there is provided a novel pumpkin variety, designated RS1090. This invention thus relates to the seeds of pumpkin variety RS1090, to the plants of pumpkin variety RS1090 and to methods for producing a pumpkin plant produced by crossing the variety RS1090 with itself or another pumpkin variety. This invention further relates to hybrid pumpkin seeds and plants produced by crossing the variety RS1090 with another pumpkin variety.

DEFINITIONS

In the description and tables which follow, a number of terms are used. In order to provide a clear and consistent understanding of the specification and claims, including the scope to be given such terms, the following definitions are provided:

Fruit—The total number of fruit harvested for a specific size category.

Average Fruit Wt.—The average weight in pounds of pumpkin fruit.

Total Wt.—The total weight in pounds of all fruit for a given size category.

Adjusted Yield per Acre—Total yield of pumpkin fruits in pounds adjusted to a per acre basis.

DETAILED DESCRIPTION OF THE INVENTION

Pumpkin variety RS1090 is a winter pumpkin of the species pepo with superior characteristics. Pumpkin variety RS1090 was developed over a 35 year period by Robert L. Majchrowski near Jackson, Mich. In the mid 1950's, the variety Connecticut Field was grown and using mass selection techniques, the best fruit were selected. As new pumpkin varieties became commercialized, these new varieties (such as Half Moon, Howden, Pankow's Field and other varieties) were planted in close proximity to the mass selected lines from Connecticut Field. Bees randomly cross pollinated these new varieties with the mass selected lines. The best fruit were selected and harvested and seed from these selected fruit were used for planting and for further selection the following year. Mass selection continued until 1989. Thereafter RS1090 plants and fruits have been selected for uniformity and have been found to breed true to type and are as uniform as other pumpkin varieties of its class.

---

VARIETY DESCRIPTION INFORMATION

Winter Pumpkin
Genus: Cucurbita
Species: Pepo
A.  Cotyledon:

Length (mm): 30
Width (mm): 12
Apex: Notched
Veining: Obscure
Color: Light green
B.  Plant:

Long vines
prickly
C.  Main Stem:

Round
Average length (cm): 305
Diameter at midpoint of first internode (mm): 22
Average number of internodes: 8
D.  Leaves:

Shape: Retuse, deep lobed
Margin: Dentate, frilled
Width (cm): 18
Length (cm): 23
Surface: blistered
Dorsal surface: glabrous
Ventral surface: bristled
Color: dark green, blotched with gray
Petiole length (cm): 25
E.  Flower - Pistillate Diameter (cm): 4
Ovary: Fisiform
Pedicel length (cm): 8
Margin: straight, frilled
Sepals width (mm): 4
Length (mm): 30

-continued
VARIETY DESCRIPTION INFORMATION

Color: orange
F. Flower - staminate:

Sepals:

width (mm): 4
  Length (mm): 22
  Pedicil length (cm): 12
  Color: orange
G. Fruit:

Length (cm): 46
  Width (cm) stem end: 37
  Width (cm) blossom end: 39
  Average weight (gm): 1310
  Shape according to variety type: Connecticut Field
  Apex: depressed
  Base: rounded
  Ribs: prominent
  Rib furrows: shallow, medium wide
  Fruit surface: smooth
  Warts: none
  Blossom scar button: depressed
H. Rind:

Thickness at medial (mm): 2
  Rind: hard
  Color pattern: regular, orange-cream
I. Flesh:

Thickness:

Blossom end (mm): 69
  Medial (mm): 66
  Stem end (mm): 69
  Texture: fine, firm, moist
  Flavor: slightly sweet
  Quality: good
  Color: yellow
J. Seed Cavity (sectioned apex to base)

Length (cm): 38
  Width (cm): 24
  Placental Tissue: abundant
  Center core: prominent
K. Fruit Stalks:

irregular, not twisted, not tapered, curved
  Length (cm): 18
  Diameter (cm): 4
  Texture: hard
  Furrows: deep
  Surface: spiny
  Attachment end: expanded
  Detaches: with difficulty
  Color: dark green
L. Seeds Length (mm): 19
  Width (mm): 12
  Thickness (mm): 25
  Face Surface: smooth
  Color: cream
  Luster: dull
  Margin: curved, rounded
  Separation from pulp: easy
  Grams per 100 seeds: 16
  No. seeds per fruit: 85

This invention is also directed to methods for producing a pumpkin variety by crossing a first parent pumpkin variety with a second parent pumpkin variety, wherein the first or second pumpkin variety is the pumpkin plant from the variety RS1090. Further, both first and second parent pumpkin plants may be from the variety RS1090. Therefore, any methods using the pumpkin variety RS1090 are part of this invention; including selfing, backcrosses, hybrid breeding, and crosses to populations. Any plants produced using pumpkin variety RS1090 as a parent are within the scope of this invention. Advantageously, the pumpkin variety is used in crosses with other pumpkin varieties to produce first generation ($F_1$) hybrid seed and plants with superior characteristics.

As used herein, the term "plant" includes plant cells, plant protoplasts, plant cell of tissue culture from which pumpkin plants can be regenerated, plant calli, plant clumps, and plant cells that are intact in plants or parts of plants, such as pollen, flowers, kernels, ears, cobs, leaves, husks, stalks, and the like.

The closest prior art to RS1090 is the pumpkin variety Pankows Field.

RS1090 is a full season field type pumpkin with a maturity of 120 days. RS1090 has a dark orange rind that is smooth with slight sutures. RS1090's shape is approximately 50% taller than its diameter and is similar in shape to Pankow's Field. In comparison to Pankow's Field, RS1090 has a much larger average fruit size being 25–35% larger. Also RS1090 is approximately 15 days later in maturity than Pankow's Field.

TABLES

In the tables that follow, the traits and characteristics of pumpkin variety RS1090 are presented. The data collected on pumpkin variety RS1090 is presented for the key characteristics and traits. Information about RS1090, as compared to several check varieties, is presented.

In Table 1 RS1090 is compared to Howden and Pankow's Field. Information for the pedigree includes:

1. Fruit—which means the number of fruit harvested in this weight category.
2. Average Fruit Weight—An average weight in pounds of all pumpkins for a given size category.
3. Total Weight—Total weight (Total Wt.) of all fruit in a size category.
4. Adjusted Yield Per Acre—Total yield of pumpkin fruits in pounds adjusted to a per acre basis.
5. Size Category—Pumpkin fruits are visually grouped together, based on their size, into a specific "size category".

In Table 1, the present invention RS1090 is compared to Howden and Pankow's Field at Fulton Farm, Troy, Ohio in 1991. RS1090 was grown to maturity, without any irrigation after germination, whereas the Howden and Pankow's Field varieties were both irrigated during their growing seasons. As Table 1 shows, even without receiving any irrigation, RS1090 had a superior total weight for each size category when compared to the irrigated varieties Howden and Pankow's Field. RS1090 had 59% higher adjusted yield per acre than Howden and was 46% higher in adjusted yield than Pankow's Field.

Table 2 contains the results of a pumpkin variety trial conducted in Bledsoe County, Tenn. during 1991 under severe drought conditions. RS1090 had a much larger average fruit weight in pounds (20.8 pounds) versus Pankow's Field (13.4 pounds) and Howden (17.8 pounds). RS1090 had the largest average fruit size of any variety of it's class and a 55% higher average fruit weight than Pankow's Field.

RS1090 has the unique and unexpected combination of larger fruit size and a larger handle (stem). The handle of RS1090 averages six inches long, is firm and sturdy and measures approximately 1.5 inches in diameter at the midpoint of the handle. RS1090's handle is 50% longer than most pumpkins in its class and 25–30% longer than the closest prior art of Pankow's Field.

Table 3 summarizes data from field trials at the University of New Hampshire during 1992. Table 3 shows RS1090 had a marketable yield advantage of 10,460 pounds greater than Pankow's Field (54,500 versus 44,040) or a 24% yield advantage. RS1090 also had an average weight advantage over Pankow's Field of 7.0 pounds, or 35% greater average weight. RS1090 had the highest average weight per pumpkin of any pumpkin variety tested in its class.

TABLE 3

1992 FIELD TRIALS AT UNIVERSITY OF NEW HAMPSHIRE

|  | TOTAL YIELD PER ACRE (In Pounds) | MARKETABLE YIELD PER ACRE LBS. (In Pounds) | AVERAGE WEIGHT PER PUMPKIN (In Pounds) |
|---|---|---|---|
| RS1090 | 64,900 | 54,500 | 27.0 |
| Pankow's Field | 65,626 | 44,040 | 20.0 |
| Connecticut Field | 81,109 | 62,185 | 21.5 |
| Thomas Halloween | 74,689 | 72,984 | 21.2 |
| Happy Jack | 53,383 | 30,250 | 15.9 |
| Autumn Gold | 67,600 | 58,715 | 14.6 |
| Ghost Rider | 57,030 | 23,855 | 12.8 |

TABLE 1

1991, FULTON FARMS, TROY, OHIO

|  | Fruit | Average Fruit Weight | Total Wt. | Adjusted Yield Per Acre in Pounds |
|---|---|---|---|---|
| RS1090, Non-Irrigated Size Category |  |  |  |  |
| 1) | 29 | 6.72 | 195 | 5,665 |
| 2) | 46 | 15.42 | 710 | 20,616 |
| 3) | 32 | 23.95 | 766 | 22,273 |
| 4) | 7 | 33.09 | 232 | 6,733 |
| 5) | 3 | 41.57 | 124 | 3,616 |
| TOTAL YIELD | 117 | 17.33 | 2028 | 58,903 |
| HOWDEN, Irrigated Size Category |  |  |  |  |
| 1) | 14 | 7.85 | 110 | 3,195 |
| 2) | 25 | 14.78 | 369 | 10,730 |
| 3) | 30 | 23.46 | 704 | 02,457 |
| 4) | 3 | 31.77 | 95 | 2,764 |
| TOTAL YIELD | 72 | 17.76 | 1278 | 37,146 |
| PANKOW'S FIELD, Irrigated Size Category |  |  |  |  |
| 1) | 29 | 6.97 | 202 | 5,876 |
| 2) | 44 | 15.43 | 679 | 19,735 |
| 3) | 21 | 22.63 | 475 | 13,804 |
| 4) | 1 | 33.10 | 33 | 960 |
| TOTAL YIELD | 95 | 14.63 | 1389 | 40,375 |

TABLE 2

PUMPKIN VARIETY TRIAL
1991
Bledsoe County, Tennessee

|  | AVERAGE FRUIT WT. | TOTAL WT. PER ACRE |
|---|---|---|
| Howden | 17.8 | 22,321 |
| RS1090 | 20.8 | 22,360 |
| Big Autumn | 12.0 | 17,736 |
| October | 14.0 | 23,198 |
| Spirit | 10.8 | 25,639 |
| Pankow's Field | 13.4 | 23,514 |

DEPOSIT INFORMATION

Variety seeds of RS1090 have been placed on deposit with the American Type Culture Collection (ATCC), Rockville, Md. 20852, under Deposit Accession Number 75368 on Nov. 25, 1992. A Plant Variety Protection Certificate is being applied for with the United States Department of Agriculture.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A pumpkin seed designated RS 1090, having ATCC accession no. 75368.
2. A plant produced by growing the seed of claim 1.
3. Pollen of the plant of claim 2.
4. Ovule of the plant of claim 2.
5. A pumpkin plant having all the physiological and morphological characteristics of the pumpkin plant of claim 2.
6. A first generation ($F_1$) hybrid pumpkin seed produced by a method of crossing a first parent pumpkin plant with a second parent pumpkin plant and harvesting the resultant $F_1$ hybrid pumpkin seed, wherein said first or second parent pumpkin plant is a pumpkin plant grown from a pumpkin seed designated RS 1090, having ATCC accession no. 75368.
7. A first generation ($F_1$) hybrid pumpkin plant produced by growing the first generation ($F_1$) hybrid pumpkin seed of claim 6.

* * * * *